United States Patent
Pflug et al.

(10) Patent No.: US 10,373,449 B2
(45) Date of Patent: Aug. 6, 2019

(54) SYSTEM AND METHOD FOR PROTECTIVE EYEWEAR

(71) Applicant: The Boeing Company, Chicago, IL (US)

(72) Inventors: William Pflug, Bellevue, WA (US); Brian Tillotson, Kent, WA (US)

(73) Assignee: THE BOEING COMPANY, Chicago, IL (US)

( * ) Notice: Subject to any disclaimer, the term of this patent is extended or adjusted under 35 U.S.C. 154(b) by 378 days.

(21) Appl. No.: 15/000,584

(22) Filed: Jan. 19, 2016

(65) Prior Publication Data

US 2017/0206753 A1     Jul. 20, 2017

(51) Int. Cl.
| G08B 23/00 | (2006.01) |
| G08B 5/36 | (2006.01) |
| G02C 7/10 | (2006.01) |
| G02C 7/12 | (2006.01) |
| A61F 9/02 | (2006.01) |

(52) U.S. Cl.
CPC ............... *G08B 5/36* (2013.01); *A61F 9/022* (2013.01); *G02C 7/101* (2013.01); *G02C 7/104* (2013.01); *G02C 7/12* (2013.01)

(58) Field of Classification Search
CPC .... A61F 9/02; F21V 23/0407; F21V 23/0478; F21V 33/0076; G02C 7/101; G02C 7/104; G02C 7/12
See application file for complete search history.

(56) References Cited

U.S. PATENT DOCUMENTS

| 5,164,707 | A  | * | 11/1992 | Rasmussen | G08B 21/18 250/221 |
| 5,760,686 | A  | * | 6/1998  | Toman     | G08B 5/006 340/331 |
| 5,914,661 | A  | * | 6/1999  | Gross     | A42B 3/046 250/206.2 |
| 6,666,630 | B2 | * | 12/2003 | Zimmermann | B23C 3/00 219/121.6 |
| 6,932,090 | B1 | * | 8/2005  | Reschke   | A61M 21/00 128/897 |
| 7,202,852 | B2 | * | 4/2007  | Harvie    | A61F 9/022 345/158 |
| 8,081,262 | B1 | * | 12/2011 | Perez     | A61F 9/023 2/8.1 |

(Continued)

OTHER PUBLICATIONS

Kieran Hunt, How Do Laser Safety Glasses Works Dec. 10, 2013.*

(Continued)

*Primary Examiner* — Quang Pham
(74) *Attorney, Agent, or Firm* — MH2 Technology Law Group LLP

(57) ABSTRACT

This disclosure is directed to increasing the use of protective eyewear in safety-critical environments. Systems and methods disclosed herein include lighting devices that emit ambient lighting and safety lighting for an environment. The safety lighting includes visible characteristics different from the ambient lighting. Additionally, the systems and methods include protective eyewear having a lens that filters out substantially the visible characteristics of the safety lighting striking the lens and pass components of the ambient light safety lighting striking the lens.

21 Claims, 3 Drawing Sheets

(56) References Cited

U.S. PATENT DOCUMENTS

| | | | | |
|---|---|---|---|---|
| 8,113,689 B2* | 2/2012 | Mayo | F42B 12/36 | 102/367 |
| 8,294,580 B2* | 10/2012 | Witwer | F16P 3/14 | 340/572.1 |
| 8,373,106 B2* | 2/2013 | Macknik | G01J 1/04 | 250/205 |
| 8,446,341 B2* | 5/2013 | Amirparviz | A61B 5/1455 | 250/221 |
| 9,489,579 B2* | 11/2016 | Matsunaga | F16P 3/142 | |
| 9,695,981 B2* | 7/2017 | Au | F16P 3/142 | |
| 9,901,125 B2* | 2/2018 | Insley | A41D 13/00 | |
| 2003/0059268 A1* | 3/2003 | Zimmermann | B23C 3/00 | 409/132 |
| 2003/0160038 A1* | 8/2003 | O'Connell | A61F 9/065 | 219/147 |
| 2004/0100384 A1* | 5/2004 | Chen | G07C 9/00111 | 340/572.1 |
| 2004/0200980 A1* | 10/2004 | Blackwell | G01N 21/643 | 250/459.1 |
| 2005/0012890 A1* | 1/2005 | Iacobucci | G02C 7/16 | 351/44 |
| 2005/0149251 A1* | 7/2005 | Donath | G01C 21/26 | 701/532 |
| 2008/0189142 A1* | 8/2008 | Brown | G06Q 10/00 | 705/4 |
| 2008/0216699 A1* | 9/2008 | McAleer | F42B 12/36 | 102/367 |
| 2009/0040014 A1* | 2/2009 | Knopf | E04G 21/32 | 340/5.1 |
| 2009/0161918 A1* | 6/2009 | Heller | G06K 9/2054 | 382/115 |
| 2009/0231417 A1* | 9/2009 | Demonchy | A61F 9/022 | 348/53 |
| 2009/0322512 A1* | 12/2009 | Frederick | G08B 3/10 | 340/539.11 |
| 2010/0231850 A1* | 9/2010 | Hones | G02C 5/126 | 351/138 |
| 2010/0245554 A1* | 9/2010 | Nam | G06T 7/0002 | 348/77 |
| 2011/0007950 A1* | 1/2011 | Deutsch | G06K 9/00624 | 382/111 |
| 2011/0043881 A1* | 2/2011 | Elferich | G02C 7/101 | 359/227 |
| 2012/0001765 A1* | 1/2012 | Boccola | G08B 21/24 | 340/686.1 |
| 2012/0088581 A1* | 4/2012 | Mao | G06K 9/00281 | 463/32 |
| 2012/0146789 A1* | 6/2012 | De Luca | G08B 21/12 | 340/540 |
| 2012/0204303 A1* | 8/2012 | Seo | A61F 9/023 | 2/12 |
| 2013/0257622 A1* | 10/2013 | Davalos | G02C 11/10 | 340/635 |
| 2013/0282609 A1* | 10/2013 | Au | F16P 3/142 | 705/325 |
| 2013/0300566 A1* | 11/2013 | Kumfer | H02H 5/12 | 340/686.6 |
| 2014/0049190 A1* | 2/2014 | Oh | H05B 37/0227 | 315/307 |
| 2014/0204331 A1* | 7/2014 | Huh | A61F 9/023 | 351/44 |
| 2015/0035437 A1* | 2/2015 | Panopoulos | F21V 14/02 | 315/112 |
| 2015/0061502 A1* | 3/2015 | Rains, Jr. | G08B 15/00 | 315/149 |
| 2016/0124225 A1* | 5/2016 | Kwak | G02B 27/0101 | 348/115 |
| 2016/0125228 A1* | 5/2016 | Son | A61B 5/442 | 382/118 |
| 2016/0217609 A1* | 7/2016 | Kornilov | G06T 15/60 | |
| 2016/0225337 A1* | 8/2016 | Ek | G09G 5/003 | |
| 2016/0232758 A1* | 8/2016 | Fletcher | G08B 3/10 | |
| 2017/0180615 A1* | 6/2017 | Lautenbach | F21V 23/003 | |
| 2017/0248272 A1* | 8/2017 | Ullrich | G06Q 10/10 | |

OTHER PUBLICATIONS

Author Unknown, "Active shutter 3D system", Wikipedia, date unknown, pp. 1-7 (accessed Dec. 3, 2015).

Kieran Hunt, "How Do Laser Safety Glasses Work?", Phillips Safety, Dec. 10, 2013, http://www.phillipssafety.com/news/howdolasersafetyglasseswork/, pp. 1-2.

Author Unknown, "Polarized 3D system", Wikipedia, date unknown, pp. 1-5 (accessed Dec. 3, 2015).

\* cited by examiner

SYSTEM AND METHOD FOR PROTECTIVE EYEWEAR

FIELD

The present disclosure generally relates to vision protection, and more particularly to improving the use of protective eyewear.

BACKGROUND

In industrial, laboratory, agricultural, and other environments, there may be objects, substances, chemicals, or emissions that can damage the eyes of individuals. Protective eyewear, such as safety glasses, has long been used to provide a physical layer of protection for a wearer's eyes. However, because of the inconvenience of carrying and/or wearing protective eyewear, individuals often fail to follow requirements that they wear such gear. For example, an individual that is working in or passing through a safety-critical work area may assume that there is little risk in not wearing protective eyewear. As a result, the individual's choice may place them at risk of injury from situations that may rapidly develop or are not immediately apparent.

SUMMARY

Systems and methods in accordance with the present disclosure include lighting devices that emit ambient lighting and safety lighting for an environment. The safety lighting includes visible characteristics different from the ambient lighting. Additionally, the systems and methods include protective eyewear having a lens that filters out substantially the visible characteristics of the safety lighting striking the lens and pass components of the ambient lighting striking the lens.

Additionally, systems and methods in accordance with the present disclosure include lighting devices that emit ambient light and safety lighting for an environment. The systems and methods also include a processor and a memory device storing program instructions that, when executed by the processor, causes the control system to perform operations including detecting a face of an individual in the environment. The operations also include determining that the face of the individual lacks protective eyewear. Further, the operations include controlling, based on the determining, the light devices to emit the safety lighting.

BRIEF DESCRIPTION OF THE DRAWINGS

The accompanying drawings, which are incorporated in and constitute a part of this specification, illustrate the present teachings and, together with the description, serve to explain the principles of the disclosure.

It should be noted that some details of the figures have been simplified and are drawn to facilitate understanding of the present teachings, rather than to maintain strict structural accuracy, detail, and scale.

DETAILED DESCRIPTION

The present disclosure generally relates to vision protection, and more particularly to increasing the use of protective eyewear. Systems, methods, and devices in accordance with the present disclosure emit safety lighting within a safety-critical environment to increase the overall use of protective eyewear. In some examples, lighting devices emit safety lighting that makes the environment uncomfortable, but not harmful, for the individuals not wearing protective eyewear specifically configured to filter the characteristics (e.g., color, polarization, intensity, and/or flashing) of the safety lighting. In some examples, a control system can dynamically activate the safety lighting to minimize its usage and effects. For example, the safety lighting may only be activated when an individual without protective eyewear is detected in the environment. Additionally, the safety lighting may be emitted in only localized areas of the environment corresponding to the current location of the individual without protective eyewear.

Figure 1:
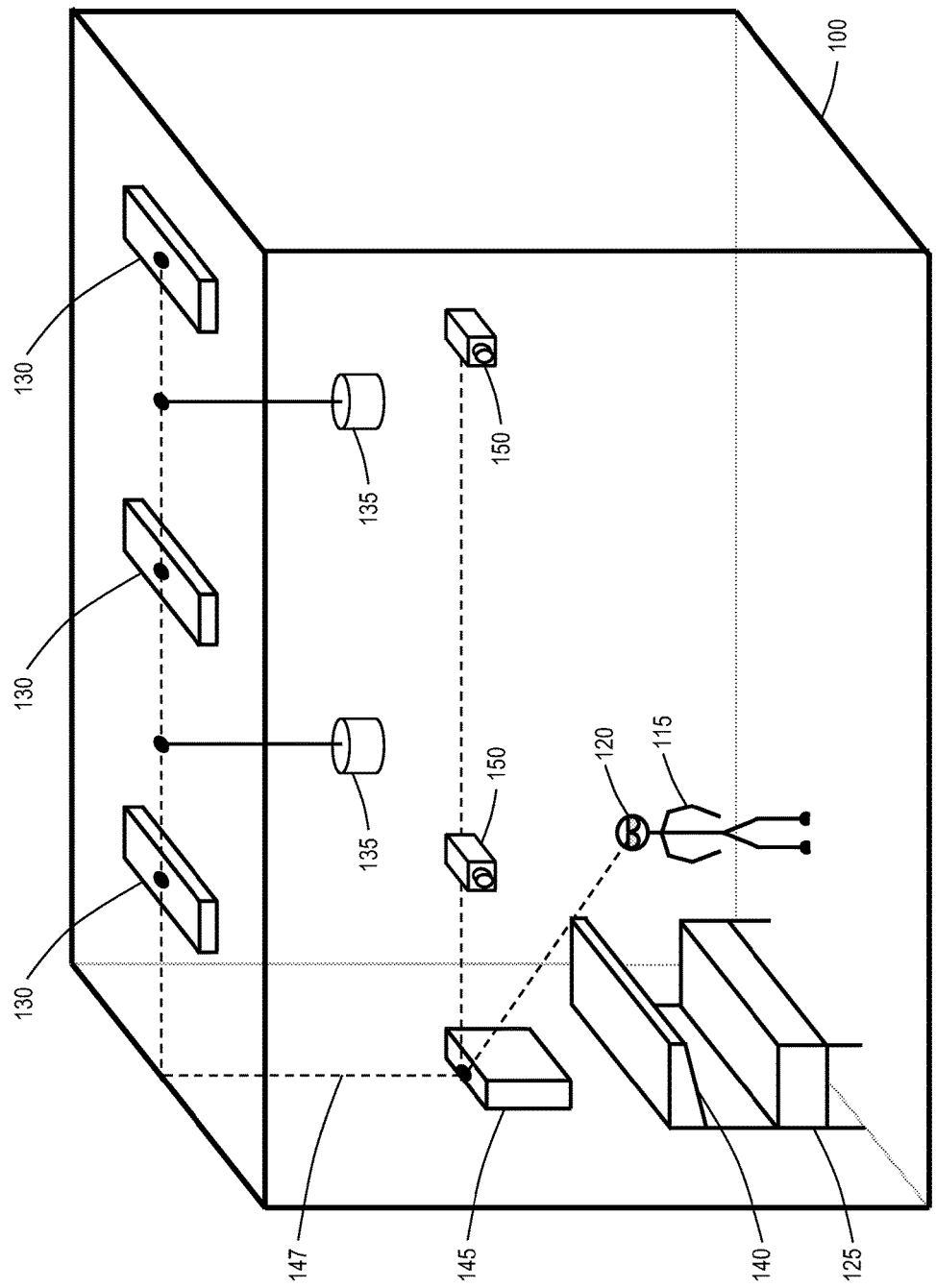
FIG. 1 illustrates a block diagram of an exemplary environment for implementing systems and processes in accordance with aspects of the disclosure.

FIG. 1 illustrates a block diagram of an exemplary environment 100 for implementing systems, processes, and devices in accordance with aspects of the disclosure. The environment 100 comprises a safety-critical space requiring individuals, such as individual 115, within the environment 100 to wear protective eyewear 120. The environment 100 can be an open or closed space, such as an airfield, a construction site, a manufacturing area, a fabrication room, a laboratory, a greenhouse, a target range, a cockpit, or any other space in which occupants are required (e.g., by laws, regulations, policies, procedures, instructions, etc.) to wear the protective eyewear 120. The individual 115 can be a worker who performs a job in the environment 100. For example, the individual 115 can be a fabricator using a workstation 125 who resides in the environment 100 for extended periods of time (e.g., more than one hour). In other cases, the individual 115 is someone who occasionally passes through or occupies the environment 100 for short periods of time (e.g., less than one minute). The protective eyewear 120 can be any apparatus having a see-through lens (or lenses) that shield a wearer's eyes from projectiles (e.g., solids and liquids) or emissions (e.g., gases and harmful light). For example, the protective eyewear 120 can be a pair of eyeglasses, goggles, a face shield, or a helmet visor.

The environment 100 includes lighting devices 130, 135, and/or 140. Some or all of the lighting devices 130, 135, and/or 140 produce ambient light within a conventional spectrum for ambient lighting (e.g., a wavelength between about 400 and about 700 nanometers). For example, the lighting devices 130, 135, and/or 140 can emit the ambient light using incandescent, fluorescent, halogen, or LED (light emitting diode) bulbs. The environment 100 may also include natural light such as sunlight. Additionally, in accordance with aspects of the present disclosure, some or all of the lighting devices 130, 135, and/or 140 produce safety lighting having one or more visible characteristics different from the ambient lighting. In examples, a radiance (e.g., optical power per unit of solid angle) of the safety lighting over some or all of the visible spectrum is substantially greater (e.g., at least 25% greater) than that of the ambient light, such that the safety lighting is uncomfortable, but not harmful, to the eyes of the individual 115 when not wearing the protective eyewear 120. In examples, the lighting devices 130, 135, and/or 140 can emit the safety lighting in a narrow spectrum range of light (e.g., between 500 nm and 550 nm, +/−10%) at an irradiance between about 0.05 Watt (W) per square meter and about 10.00 W per square meter at the expected distance of the individual 115 with respect to the lighting devices 130, 135, and/or 140, which is below an intensity that can cause damage. Additionally or alternatively, the lighting devices 130, 135, and/or 140 can periodically flash (e.g., strobe) the safety lighting at a frequency that is uncomfortable, but not harmful, to the individual 115 when without the protective eyewear 120. For example, the lighting devices 130, 135, and/or 140 can flash at a frequency between 1 Hertz (Hz) to about 12 Hz, which is below frequencies that can induce seizures.

The lighting devices 130, 135, and/or 140 function together to flood the entire environment 100 with ambient lighting and safety lighting. For example, the lighting devices 130 can flood the environment 100 with the ambient lighting, and the lighting devices 135 can flood the environment 100 with the safety lighting. In other examples, the lighting devices 130 can flood the environment 100 with the ambient lighting, and the lighting devices 135 and/or 140 can be selectively activated based on a location of the individual 115 to provide the safety lighting only at a portion of the environment 100.

In an exemplary implementation of an example consistent with the present disclosure, the lighting devices 130, 135 and/or 140 can be green light emitting diodes (LEDs) mounted on a wall or other object (e.g., workstation 125) of the environment 100 and configured to generate 5 W of optical power over one steradian of solid angle. As such, at a distance of one meter from the lighting devices 130, 135 and/or 140, the irradiance would be about 5 W per square meter, which would be very uncomfortable for the individual 115 looking at the lighting devices 130, 135 and/or 140, but not harmful or dangerous. At a distance of 10 meters from the lighting devices 130, 135 and/or 140, the irradiance would be about 0.05 W per square meter, which would still be uncomfortable for the individual 115. Notably, the apertures of the LEDs can be sized to protect the individual 115 from harm if the individual 115 moves close (e.g., within one meter) to the lighting devices 130, 135 and/or 140 of the present example. For example, the LED (or cluster of LEDs) can have an aperture of about 10 millimeters in diameter. From a distance of 10 meters, the LEDs have an angular diameter of 1 mrad (milliradian). An exemplary LED (or clusters of LEDs) can have an aperture of about 10 millimeters in diameter. From a distance of 10 meters, this LED would have an angular diameter of 1 mrad. Because light sources wider than 1.5 mrad are considered "extended sources" (rather than "point sources"), such extended sources can safely (and comfortably) emit more light than point sources. That is, the maximum permissible exposure to an extended source increases linearly with angle above 1.5 mrad. Thus, at 10 meters the irradiance of the LEDs 0.05 W per square meter comes from a source less than 1.5 mrad wide (i.e., a point-like source) and would therefore uncomfortable. At one meter, the LED appears to be 10 mrad wide. This width is greater than 1.5 mrad by a factor of 6.67, so the maximum permissible exposure would be 66.7 W per square meter and the threshold of discomfort is 0.333 W per square meter. The LED's irradiance of 5 W per square meter at a one meter distance would be uncomfortable but safe. At 10 cm distance, the irradiance is 500 W per square meter and the angular width of the LED is 100 mrad. At that width, the maximum permissible exposure is 667 watts per square meter. Light reaching the individual 115 from sources wider than 100 mrad (i.e. at locations closer than 10 cm in this example) does not increase danger to the eye, so even if the individual 115 was extremely close to the LED, no injury would occur. Thus, the size of the optical aperture of the lighting devices 130, 135, and/or 140 can provide safety lighting having an irradiance that is below a maximum permissible exposure at any distance.

The exemplary implementation above uses green light for the sake of example. Other implementations consistent with the present disclosure can use lighting devices 130, 135 and/or 140 that emit wavelengths corresponding to other colors of light (i.e. not near 550 nm). In such implementations, it is understood the lighting devices 130, 135, and/or 140 can be configured to generate higher optical power sufficient to compensate for the reduced photopic luminous efficiency of the wavelength relative to green light, for which human visual sensitivity is strongest.

Still referring to FIG. 1, the protective eyewear 120 includes a lens (or lenses) that filters out substantially all the visible characteristics of the safety lighting striking the lens, while passing a substantial amount of the ambient lighting. The protective eyewear 120 passively removes the safety lighting produced by the lighting devices 130, 135, and/or 140. In some examples, the safety lighting produced by the lighting devices 130, 135 and/or 140 produce an uncomfortably bright light consisting essentially of a narrow spectrum range (e.g., green light having a wavelength between about 500 nm and about 550 nm). In such examples, the lens of the protective eyewear 120 can comprise an optical color filter that removes substantially all light in the narrow spectrum range of the safety light. Additionally or alternatively, in some examples, the safety lighting produced by the lighting devices 130, 135, and/or 140 consists essentially of an uncomfortably bright, highly-polarized light. In such examples, the lens of the protective eyewear 120 can be a polarized optical filter that removes substantially all of the polarized light.

Figure 2:
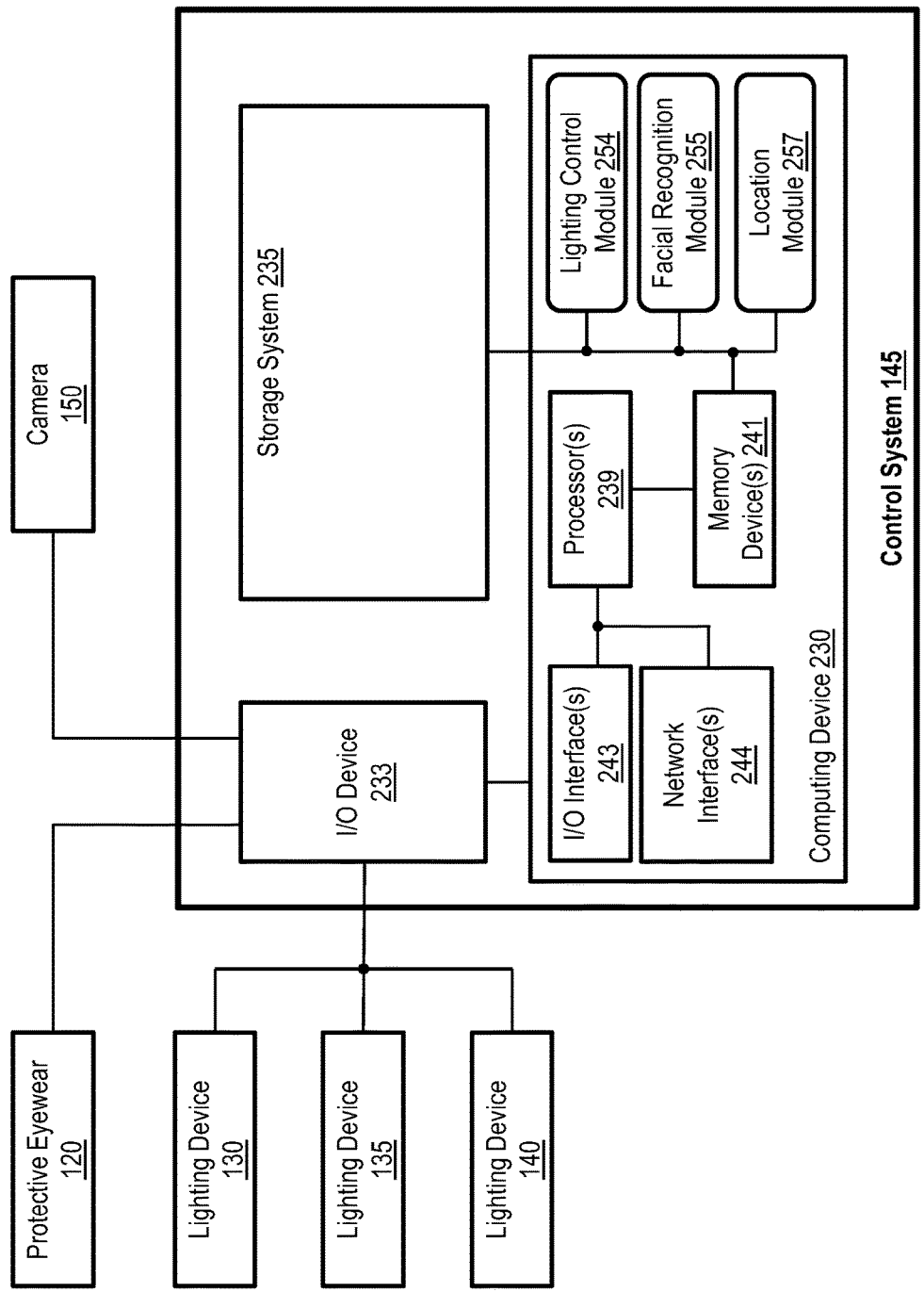
FIG. 2 illustrates a block diagram of an exemplary control system in accordance with aspects of the present disclosure.

In examples consistent with aspects of the present disclosure, the environment 100 includes a control system 145 that communicatively links with and actively controls the protective eyewear 120 and the lighting devices 130, 135, and/or 140 via one or more wired or wireless communication channels 147. As shown in FIG. 2, the control system 145 can be a single, standalone device. However, it is understood that one or more control systems 145 can be integrated with or distributed among the lighting devices 130, 135 and/or 140, and networked via communication channels 147 to provide the functionality disclosed herein. In some examples, the safety lighting produced by the lighting devices 130, 135, and/or 140 is an uncomfortably bright light that flashes (e.g., at regular or irregular intervals or frequencies) that can be selectively determined by the control system 145. The lens (or lenses) of the protective eyewear 120 can use an active shutter system configured to filter the flashing light by shuttering the lens in substantial synchronicity with the flashing of the safety light based on the control system 145 or the lighting devices 130, 135, and/or 140 transmitting synchronization information describing the rate of the flashing to the protective eyewear 120.

Further, in accordance with aspects of the present disclosure, the environment 100 includes one or more cameras 150, which are communicatively linked to the control system 145 via one or more communication channels 147, for detecting whether or not the individual 115 is wearing the protective eyewear 120. In examples, the control system 145 can use facial recognition techniques to determine whether the individual 115 is wearing the protective eyewear 120. If the control system 145 determines that the individual 115 is not wearing the protective eyewear 120 on their face, then the control system 145 may control the lighting devices 135 and/or 140 to produce the safety lighting and, thereby induce the individual 115 to wear the protective eyewear 120. In examples, the lenses of the cameras 150 can include filters that are the same or similar to those described above with regard to the protective eyewear 120 to prevent the safety lighting from affecting images captured by the cameras 150. Additionally or alternatively, the cameras 150 can capture images in a spectrum (e.g., 900-14,000 nanometers) that is outside the visible spectrum range of the safety lighting produced by the lighting devices 130, 135, and/or 140.

Still further, in accordance with aspects of the present disclosure, the control system 145 may track the location of the individuals 115 in the environment 100 and selectively activate individual one of the lighting devices 130, 135, and/or 140 to emit safety lighting based on the current location of the individual 115. For example, the control system 145 can detect that the individual 115 is positioned at or near the workstation 125 and is not wearing the protective eyewear 120. Accordingly, the control system 145 can activate the lighting device 140 at the workstation 125 to produce the safety lighting, which the individual 115 can avoid by wearing the protective eyewear 120. By doing so, the control system 145 minimizes the effect of the safety lighting by only activating a single light source, rather than all of the lighting devices 135. Further, doing so prevents the individual 115 from avoiding the safety lighting.

Still further, in accordance with aspects of the present disclosure, the control system 145 can selectively increase the safety lighting produced by the lighting devices 130, 135 and/or 140 over time such that the effects on the individual 115 are progressively increased until the control system 145 detects that the individual 115 is wearing the protective eyewear 120, or safety lighting reaches a maximum intensity. For example, if the control system 145 initially determines that the individual 115 is in the environment 100 and is not wearing the protective eyewear 120, then the control system 145 can cause one or more of the lighting devices 130, 135 and/or 140 to generate the safety lighting at a first level (e.g., 0.05 W per square meter) and/or at a first rate of flashing (e.g., no initial flashing). After a first predetermined amount of time (e.g., about 15 seconds), if the control system 145 determines that the individual 115 is in the environment 100 and is still not wearing the protective eyewear 120, then the control system can cause one or more of the lighting devices 130, 135, and/or 140 to increase the safety lighting to a second intensity (e.g., 0.5 W per square meter) and/or at a second rate of flashing (e.g., 1.0 Hz). And, after a second predetermined amount of time (e.g., an additional 15 seconds), if the control system 145 determines that the individual 115 is still not wearing the protective eyewear 120, then the control system can cause one or more of the lighting devices 130, 135, and/or 140 to increase the safety lighting to a third intensity (e.g., 5.0 W per squire meter) and/or at a third rate of flashing (e.g., 10 Hz). Hence, the control system 145 can actively control the impact of the safety lighting on the individual 115. By doing so, the control system 145 minimizes energy consumption. Also, the active control minimizes or terminates the effect of the safety lighting on the individual 115 based on compliance. Moreover, the active control prevents the individual 115 from becoming habituated to a single intensity of the safety lighting.

FIG. 2 illustrates a block diagram of an exemplary control system 145 in accordance with aspects of the present disclosure. The control system 145 includes hardware and software that perform processes and functions described herein. In particular, the control system 145 can include at least one computing device 230, at least one input/output (I/O) device 233, and at least one storage system 235. The I/O device 233 can include any device that enables a user (e.g., an operator) to interact with the control system 145 (e.g., via a user interface) and/or any device that enables the computing device 230 to communicate with one or more other devices and/or information networks using any type of data communications link (e.g., communication channel 147). For example, the I/O device 233 can include a touchscreen display, pointer device, keyboard, etc. Additionally, in accordance with aspects of the present disclosure, the I/O device can communicate with one or more sets of protective eyewear 120, one or more lighting devices 130, 135, and 140, and one or more cameras 150, which can be the same or similar to those previously described herein. The storage system 235 can comprise a computer-readable hardware storage device that stores information and program instructions. For example, the storage system 235 can be one or more flash drives and/or hard disk drives.

The computing device 230 includes one or more processors 239 (e.g., microprocessor, microchip, or application-specific integrated circuit), one or more memory devices 241 (e.g., random access memory and read only memory), one or more I/O interfaces 243, and one or more network interfaces 244. The memory device 241 can include a local memory (e.g., a random access memory and a cache memory) employed during execution of program instructions. Additionally, the computing device 230 includes at least one communication channel (e.g., a data bus) by which it communicates with the I/O device 233, and the storage system 235. The processor 239 executes computer program instructions (e.g., an operating system and/or application programs), which can be stored in the memory device 241 and/or storage system 235. Moreover, the processor 239 can execute computer program instructions of a lighting control module 254, a facial recognition module 255, and a location module 257. The lighting control module 254 can control the lighting devices 130, 135, and/or 140 to selectively activate the ambient lighting and the safety lighting. Additionally, the lighting control module 254 can control the lighting devices 130, 135, and/or 140 to modify the visible characteristics (e.g., intensity and flashing) of the safety lighting as previously described herein. The facial recognition module 255 and location module 257 can be surveillance software configured to and/or trained (e.g., via machine learning) to track individuals and detect the protective eyewear.

It is noted that in some examples the computing device 230 can comprise any general-purpose computing article of manufacture capable of executing computer program instructions installed thereon (e.g., a personal computer, server, application-specific integrated circuit computer, etc.). However, the computing device 230 is only representative of various possible equivalent-computing devices that can be configure by program instructions into a special-purpose machine that performs the processes and functions described herein. To this extent, in examples, the functionality provided by the computing device 230 can be any combination of general and/or specific purpose hardware and/or computer program instructions. In each example, the program instructions and hardware can be created using standard programming and engineering techniques, respectively.

Figure 3:
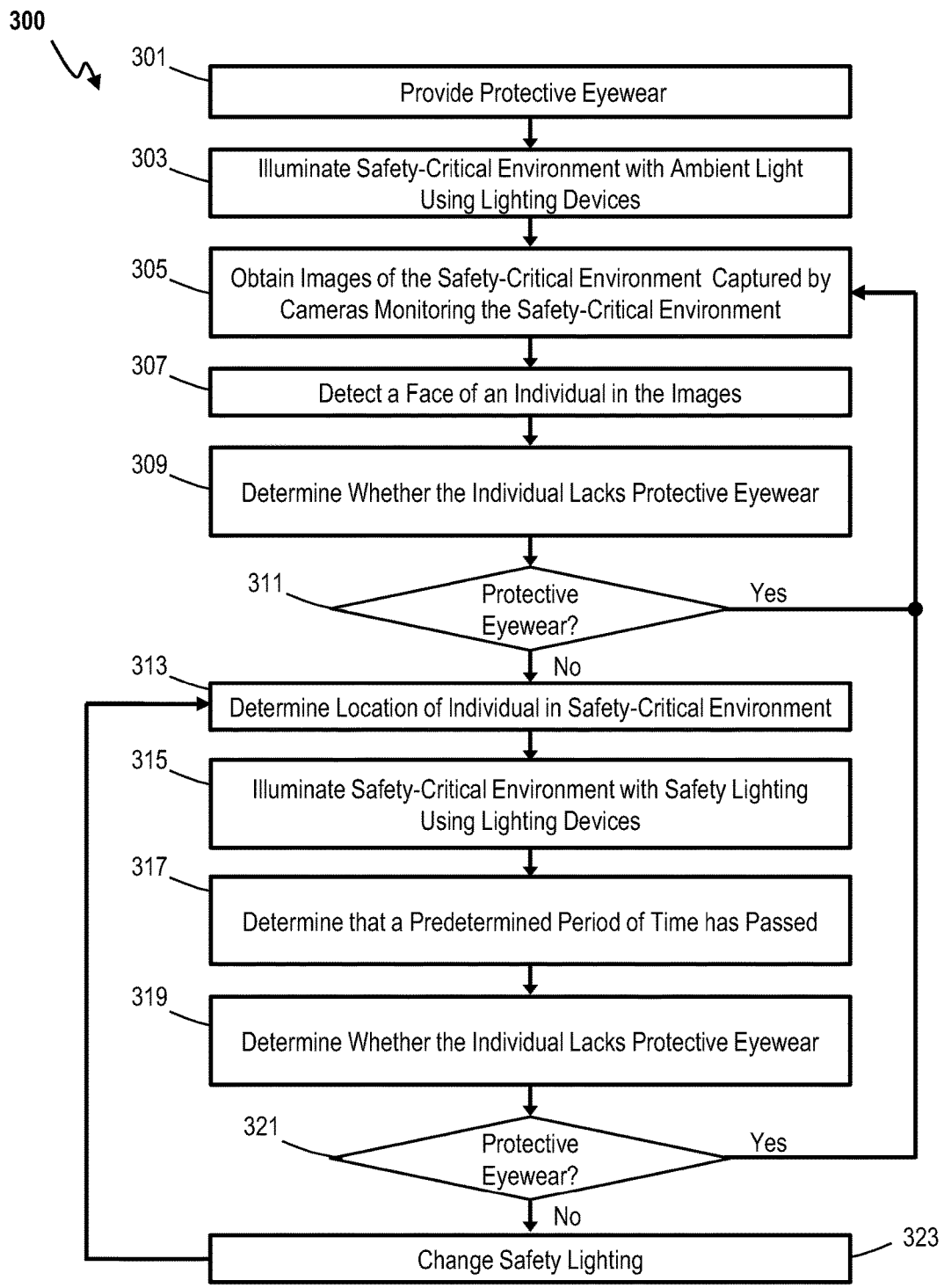
FIG. 3 illustrates a flow diagram of an exemplary process for improving usage of protective eyewear in accordance with aspects of the present disclosure.

The flow diagram in FIG. 3 illustrates an example of the functionality and operation of a possible implementation of systems, devices, methods, and computer program products according to various examples of the present disclosure. Each block in the flow diagram of FIG. 3 can represent a module, segment, or portion of program instructions, which includes one or more computer executable instructions for implementing the illustrated functions and operations. In some alternative implementations, the functions and/or operations illustrated in a particular block of the flow diagram can occur out of the order shown in FIG. 3. For example, two blocks shown in succession can be executed substantially concurrently, or the blocks can sometimes be executed in the reverse order, depending upon the functionality involved. It will also be noted that each block of the flow diagram and combinations of blocks in the block can be implemented by special purpose hardware-based systems that perform the specified functions or acts, or combinations of special purpose hardware and computer instructions.

FIG. 3 illustrates a flow diagram of an exemplary process for improving the use of protective eyewear in accordance with aspects of the present disclosure. At 301 one or more individuals (e.g., individual 115) are provided with protective eyewear (e.g., protective eyewear 120) for a safety-critical space (e.g., environment 100). At 303 the safety-critical space is illuminated with ambient light from one or more lighting devices (e.g., lighting devices 130, 135, and/or 140). At 305 a computing device (e.g., control system 145 executing facial recognition module 255 and/or location module 257) obtains images of the safety-critical space captured by one or more cameras (e.g., cameras 150) that monitor the safety-critical space and tracks individuals therein. For example, the cameras can provide substantially constant surveillance of the safety-critical space allowing the computing device to perform real-time or near real-time detection and analysis of images provided by the cameras. At 307 the computing device detects a face of an individual (e.g., individual 115) in one or more of the images obtained at 305 and, at 309 determines whether the individual detected at 307 lacks protective eyewear. At 311, if it is determined at 309 that the individual is wearing the protective eyewear, then the process 300 iteratively returns to obtains images of the safety-critical space at 305. If it is determined at 309 that the individual is not wearing the protective eyewear, then at 313 the computing system (e.g., executing location module 257) can determine the location of the individual. At 315, the computing system (e.g., executing lighting control module 254) illuminates the safety-critical environment with safety lighting using one or more of the lighting devices. In examples, only lighting devices at or near the location determined at 313 are illuminated to minimize the effects of the safety lighting.

In some examples, at 317 the computing device (e.g., using lighting control module 254) determines that a predetermined amount of time has passed since causing the one or more of the plurality of light devices to emit the safety lighting at 315. After 317, the computing device (e.g., using facial recognition module 255) determines whether the individual still lacks the protective eyewear in a manner which is the same or similar to 305, 307 and 309 above. At 321, if it is determined at 319 that the individual is wearing the protective eyewear, then the process 300 iteratively returns to obtaining images of the safety-critical space at 305. If it is determined at 319 that the individual is not wearing the protective eyewear, then at 323 the computing system (e.g., executing lighting control module 254) changes the safety lighting emitted by the one or more of the plurality of lighting devices as described previously herein. For example, the intensity or strobe of the safety lighting can be incrementally increased. The process 300 then returns to 313, wherein the location of the individual is determined and the safety-critical environment can be illuminated at 315 by safety lighting corresponding to the location, as increased at 323.

As detailed above, implementations of the examples disclosed above improve the use of protective eyewear in safety-critical environments by inducing individuals to wear their protective eyewear using safety lighting that is bothersome, but not harmful. Advantageously, the examples disclosed herein prevent individuals from becoming habituated to the safety lighting because it is not visible if the individual is wearing the protective eyewear while being visible without the protective eyewear. Further, some examples may avoid habituation by actively increasing the intensity of the safety lighting The present disclosure is not to be limited in terms of the particular examples described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A system comprising:
    a plurality of lighting devices configured to emit ambient lighting and safety lighting for an environment, the safety lighting comprising one or more visible characteristics different from the ambient lighting;
    a processor; and
    a memory device storing program instructions that, when executed by the processor, causes the system to perform operations comprising:
        detecting a face of an individual in the environment;
        determining that the face of the individual lacks protective eyewear; determining a first location of the individual in the environment;
        selectively activating a first lighting device of the plurality of lighting devices corresponding to the first location of the individual to emit the safety lighting at a first intensity;
        selectively increasing the safety lighting produced by the first lighting device over time such that effects of the safety lighting on the individual are progressively increased in response to the determining that the individual lacks of the protective eyewear during emitting of the safety lighting;
        determining that the individual is wearing the protective eyewear during emitting of the safety lighting; and
        minimizing or terminating the safety lighting produced by the plurality of lighting devices in response to determining whether the individual is wearing the protective eyewear during emitting of the safety lighting.

2. The system of claim 1, wherein the one or more visible characteristics of the safety lighting emitted by the plurality of lighting devices comprises flashing.

3. The system of claim 2, wherein the flashing of the safety lighting occurs in a range from about 1 Hertz (Hz) to about 12 Hz.

4. The system of claim 1, wherein the one or more visible characteristics of the safety lighting emitted by the plurality of lighting devices comprises a intensity of the safety lighting substantially greater than an intensity of the ambient light.

5. The system of claim 1, wherein a size of an optical aperture of the safety lighting provides an irradiance below a maximum permissible exposure at any distance.

6. The system of claim 1, further comprising:
    protective eyewear including a lens configured to filter out substantially all of the one or more visible characteristics of the safety lighting striking the lens and pass components of the ambient lighting striking the lens, wherein:
        the safety lighting emitted by the plurality of lighting devices consists essentially of polarized light; and
        the lens of the protective eyewear comprises a polarized optical filter configured to remove the polarized light.

7. The system of claim 6, wherein:
    the safety lighting emitted by the plurality of lighting devices consists essentially of a narrow spectrum range of light; and
    the lens of the protective eyewear comprises an optical color filter that removes the narrow spectrum range of light.

8. The system of claim 6, wherein:
    the safety lighting emitted by the plurality of lighting devices comprises a flashing light; and
    the lens of the protective eyewear comprises an active shutter system configured to filter the flashing light based on information communicated to the protective eyewear.

9. The system of claim 1, wherein the plurality of lighting devices are configured to flood the environment with the ambient light and direct the safety lighting to a particular portion of the environment.

10. The system of claim 1, wherein the operations further comprise:
    determining a second location of the individual in the environment;
    determining that the face of the individual lacks the protective eyewear; and
    selectively activating a second lighting device of the plurality of lighting devices corresponding to the second location of the individual to emit the safety lighting at a second intensity.

11. A system comprising:
    a plurality of lighting devices configured to emit ambient lighting and safety lighting for an environment; and
    a processor and a memory device storing program instructions that, when executed by the processor, causes the system to perform operations comprising:
        detecting a face of an individual in the environment;
        determining that the face of the individual lacks protective eyewear;
        controlling, based on the determining, one or more of the plurality of lighting devices to emit the safety lighting;
        iteratively determining whether the face of the individual is wearing protective eyewear during emitting of the safety lighting;

based on determining that the individual is not wearing the protective eyewear during emitting of the safety lighting, increasing the safety lighting produced by the plurality of lighting devices over time such that effects of the safety lighting on the individual are progressively increased; and based on the determining that the individual is wearing the protective eyewear during the emitting of the safety lighting, minimizing or terminating the safety lighting produced by the plurality of lighting devices.

12. The system of claim 11, wherein the operations further comprise:

determining that a predetermined amount of time has passed since causing the one or more of the plurality of light devices to emit the safety lighting; and modifying the safety lighting emitted one or more of the plurality of lighting devices.

13. The system of claim 12, wherein modifying the safety lighting comprises increasing an intensity of the safety lighting.

14. The system of claim 12, wherein modifying the safety lighting comprises increasing a rate of flashing of the safety lighting.

15. The system of claim 14, wherein the operations further comprise transmitting synchronization information describing the rate of flashing of the safety lighting to protective eyewear.

16. The system of claim 11, wherein the operations further comprise:

detecting the individual comprises determining a location of the individual in the environment; and causing one or more of the plurality of lighting devices to emit the safety lighting comprises activating the one or more of the plurality of lighting devices at or near the location of the individual.

17. A method for increasing a use of protective eyewear in an environment, the method comprising:

illuminating, by a computing device, the environment with ambient light using a plurality of lighting devices;

obtaining, by the computing device, images of the environment captured by one or more cameras monitoring the environment;

detecting, by the computing device, a face of an individual in one or more of the images;

determining, by the computing device, that the individual lacks protective eyewear;

controlling, by the computing, device, one or more of the plurality of lighting devices to emit safety lighting based on the determining;

iteratively determining, by the computing device, whether the face of the individual is wearing the protective eyewear during emitting of the safety lighting;

based on determining that the individual is not wearing the protective eyewear during emitting of the safety lighting, increasing the safety lighting produced by the plurality of lighting devices over time such that effects of the safety lighting on the individual are progressively increased;

iteratively determining, by the computing device, that the face of the individual is wearing protective eyewear during emitting of the safety lighting; and minimizing or terminating, by the computing device, the safety lighting produced by the plurality of devices based on the determining that the individual is wearing the protective eyewear during the emitting of the safety lighting.

18. The method of claim 17, further comprising determining, by the computing device, that a predetermined amount of time has passed since causing the one or more of the plurality of lighting devices to emit the safety lighting;

determining, by the computing device, that the individual lacks the protective eyewear; and increasing, by the computing device, the safety lighting emitted by the one or more of the plurality of lighting devices.

19. The method of claim 18, wherein increasing the safety lighting emitted by the one or more of the plurality of lighting devices comprises increasing an intensity of the safety lighting.

20. The method of claim 18, wherein:

increasing the safety lighting emitted by the one or more of the plurality of lighting devices comprises increasing a rate of flashing of the safety lighting; and the method further comprises transmitting synchronization information describing the rate of the flashing to protective eyewear via a communication channel.

21. The method of claim 17 further comprising:

detecting, by the computing device, the individual comprises determining a location of the individual in the environment; and causing, by the computing device, one or more of the plurality of lighting devices to emit the safety lighting comprises activating a first light of the one or more of the plurality of lighting devices at or near the location of the individual.

\* \* \* \* \*